United States Patent [19]

Freundlich

[11] Patent Number: 4,653,907
[45] Date of Patent: Mar. 31, 1987

[54] BLOOD CULTURE BOTTLE EXAMINING INSTRUMENT

[76] Inventor: Lawrence F. Freundlich, 923 N. First St., New Hyde Park, N.Y. 11040

[21] Appl. No.: 743,675

[22] Filed: Jun. 11, 1985

[51] Int. Cl.[4] .................. G01N 33/48; G01N 21/85
[52] U.S. Cl. ..................................... 356/39; 356/244; 356/427
[58] Field of Search ............... 356/240, 244, 426, 427, 356/428, 39; 350/523, 525, 532

[56] References Cited

U.S. PATENT DOCUMENTS

| | | | |
|---|---|---|---|
| 2,920,524 | 1/1960 | Bartlett et al. | 356/426 X |
| 3,652,169 | 3/1972 | Danti et al. | 356/244 |
| 3,992,096 | 11/1976 | Oliveira | 356/244 X |

FOREIGN PATENT DOCUMENTS

| | | | |
|---|---|---|---|
| 969775 | 12/1950 | France | 356/240 |
| 909038 | 10/1962 | United Kingdom | 356/427 |

OTHER PUBLICATIONS

Ealing 84/85 Optics Catalog, Copyright 1985, The Ealing Corp, USA, pp. 84 & 95.

*Primary Examiner*—Vincent P. McGraw
*Attorney, Agent, or Firm*—Nicholas J. Garofalo

[57] ABSTRACT

An instrument for making a visual examination of a blood culture bottle for the presence of microorganisms, the instrument having an elongated base on which is mounted a platform defining a seat for the bottle to be examined, a light source rearwardly of the platform for illuminating the bottle, a combined viewing and magnifying lens forwardly of the platform for magnifying the bottle to a viewer, and a manipulative control knob drivingly connected with the platform for rotating the latter while the bottle thereon is being viewed, both the light source and lens being arranged for focusing downward upon the bottle and platform.

10 Claims, 7 Drawing Figures

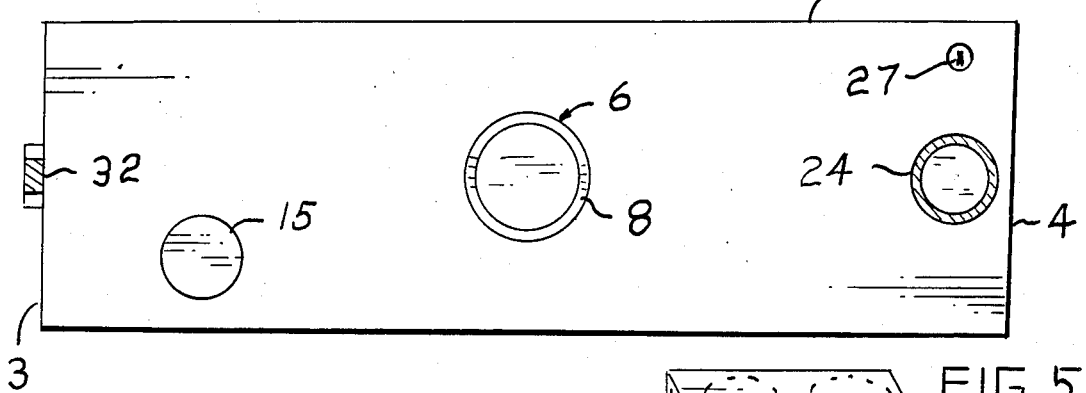
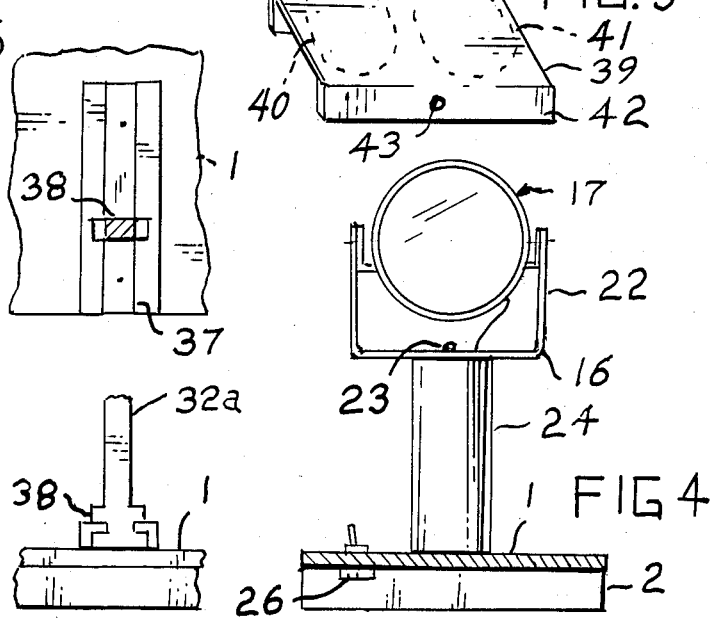
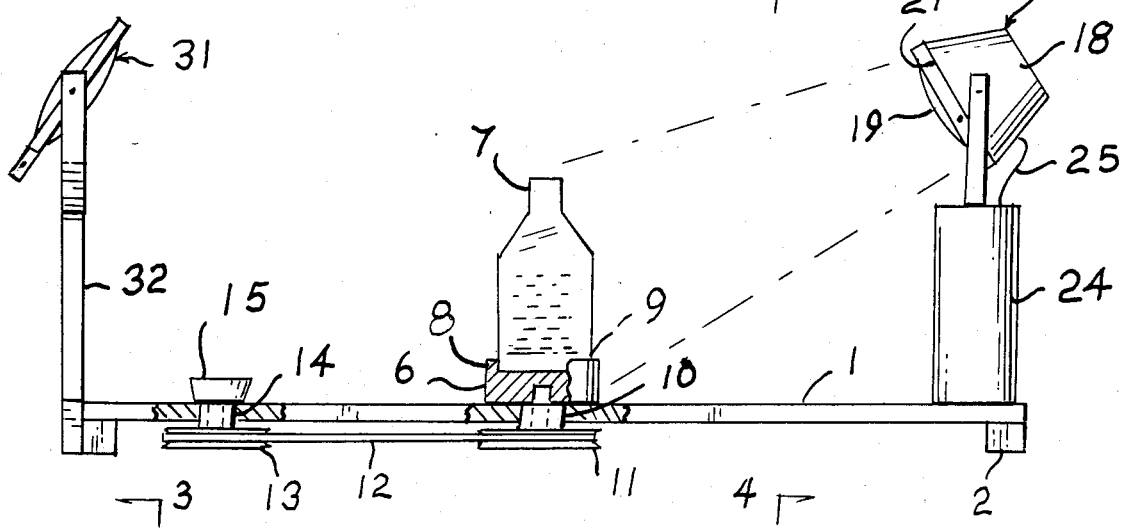

BLOOD CULTURE BOTTLE EXAMINING INSTRUMENT

BACKGROUND OF THE INVENTION

This invention is directed, in general, to means for subjecting blood culture bottles to visual examination for the growth of bacteria. More particularly, it is concerned with an instrument which is especially suited to enabling a blood culture bottle to be efficiently visually examined with reasonable assurance of detecting the presense, if any, of bacteria cultivated therein.

What is commonly termed a blood culture bottle is known as a bottle of clear transparent glass containing a liquid media of nutrients suitable for the cultivation of microorganisms, especially bacteria, that may be present in a blood specimen injected into the bottle.

It has long been a custom in making an examination of a blood culture bottle to manually hold it before a light and, while viewing the contents therein, to manipulate the bottle with the holding hand so as to bring various areas of the bottle before the eyes of the examiner.

This mode of examination has its faults, because of which the examination could at times fall short of being thorough. The presence of some bacterial growth in the bottle might accordingly escape detection. During the examination the bottle should be rotated a full 360° because, at times, bacteria may have developed in a clump, a small cluster or a speck floating in suspension in some area of the media. But, the human hand is mechanically unable to be twisted enough to carry the bottle full circle. Accordingly, the examiner in using this conventional method will resort to various manipulations of the bottle in an effort to bring all areas of the bottle into view. Nevertheless, a shadow cast by the examiner's fingers or hand on the bottle or a cloud created within the bottle by hemolysis, together with poor illumination and a lack of magnification of the bottle could cause misleading readings or a failure to detect the presence of some bacterial growth.

A proper examination with close scrutiny of a blood culture bottle for bacterial growth is at all times a necessity in the interests of the patient concerned. Even a small degree of bacterial growth escaping the eye of the examiner could prove detrimental to a proper diagnosis and treatment of the ills of a patient.

Accordingly, the general object of this invention is to provide an instrument or device for enabling a visual examination of a blood culture bottle in a manner which is convenient, thorough, and avoids the faults associated with the customary method of manually holding the bottle before a light.

A more particular object of the invention is to provide a small hand-portable instrument which enables a visual examination of a blood culture bottle with a high degree of assurance to the examiner of detecting signs of bacterial growth, if any, in the contents of the bottle.

A further object of the invention is to provide an instrument for the examination of a blood culture bottle, on which instrument the bottle is seated upon a rotatable platform in favorable illumination, and is viewable by the examiner with both eyes through a magnifying lens.

Another object is to provide such an instrument wherein the illumination of the bottle is directed downward away from the eyes of the viewer.

The foregoing objects as well as others will become apparent as this specification continues in further detail.

BRIEF SUMMARY OF THE INVENTION

In accordance with the invention there is provided a hand-portable instrument which, as a unit, includes a base in the form of a panel upon which the various components of the unit are supported.

Mounted upon the base between a source of light and a combined viewing and magnifying lens is a rotatable platform. A blood culture bottle is adapted to be seated upon the platform for inspection as to whether any bacterial growth has developed therein. The light source is mounted on the panel at one end thereof. It is adapted to be pivotally adjusted or focused to illuminate or envelope the bottle with a revealing degree of light.

The viewing and magnifying lens is mounted on the panel at the opposite end thereof. It is adapted to be adjustably pivoted and focused relative to the bottle so as to enlarge the latter to a desireable revealing degree to the eyes of the examiner.

A manually operable control knob, mounted upon the panel, operatively connects with the platform, whereby the latter may be progressively rotated through 360° while under the scrutiny of the examiner. The control knob is located where the examiner's controling hand will not cast any undesirable shading upon the bottle or interfere with its magnification.

The foregoing structure of the invention, its features and advantages will become increasingly apparent as this specification unfolds in greater detail and as it is read in conjunction with the accompanying drawing. However, it is to be expressly understood that the drawing is for purposes of illustration and description, and it is not to be construed as limiting the scope of the invention.

BRIEF DESCRIPTION OF THE DRAWING

In the accompanying drawing:

FIG. 1 is a side elevation view of an instrument embodying the invention with some portions broken away;

FIG. 2 is a plan view of the supporting panel with portions of the viewing and magnifying means and the illuminating means broken away;

FIG. 3 is a section taken on line 3—3 of FIG. 1;

FIG. 4 is a section taken on line 4—4 of FIG. 1;

FIG. 5 is a perspective view of a dual bottle seating platform adapted to be clamped over the existing single bottle platform;

FIG. 6 is a fragmentary detail of the panel as being provided with a keyway on which the viewing and magnifying lens unit may be slidably mounted; and FIG. 7 is a detail showing a modification of the supporting stem of the viewing and magnifying lens unit as keyed for slidable movement along the keyway.

DETAILED DESCRIPTION OF THE INVENTION

The instrument embodying the invention, as illustrated in the drawing, is a unitary device. It has a base in the form of a rectangular panel 1 which serves as a support for the various components of the instrument. A pair of strips or ribs 2, one of which is fixed along the underside of the front end 3 of the panel and the other of which is fixed along the underside of the rear end 4 of the panel, serve as feet for the instrument and create a desireable space at the underside of the panel.

Centrally of the surface of the panel is mounted a rotatable platform 6. It defines an annular seat upon which a conventional blood culture bottle 7 may be rested for examination as to its contents. An annular slightly raised lip 8 about the seat serves as a guide. It enables a quick seating of the bottle and also serves to restrain the bottle on the seat against accidental displacement. The lip is of slight elevation, being raised less than the normal thickness of the glass defining the bottom 9 of the bottle, so that the contents of the bottle remain visible above and clear of the lip. The bottle shown here by way of illustration has a circular body complementing the seat defined by the lip.

The platform 6 is rotatable by manually operable means. To this end, the platform is secured to a pin depending through a bearing 10 in the panel to the space below. A pulley 11, fixed to the pin below the panel, is connected by a belt 12 with a second pulley 13. The latter is fixed to the lower end of a pin extending through a bearing 14 to the upper side of the panel. A control knob 15, secured to the upper end of the latter pin, is manually rotatable in either direction to effect through the pulleys and belt turning of the platform through 360°.

Mounted on a fork 16 at the rear of the panel is a light source unit 17 (FIGS. 1, 4). It includes a cowl or shell 18 in which an electric lamp 19 is contained. The lamp is entered through the open front end of the shell, and is retained therein by set screws 21. The unit is pivoted between upraised arms 22 of the fork upon a pair of pins defining a horizontal axis. The fork in turn is swiveled on a vertical axis defined by a pin 23 mounted centrally of a support 24 secured to the surface of the panel.

The lamp 19 is preferably of a type adapted to cast a spotlight on the bottle being examined. I find a sealed beam lamp suitable for this purpose. The light source unit may, as needed, be adjustably swiveled about its vertical axis and adjustably pivoted about its horizontal axis to a position where it illuminates and envelopes the entire bottle and its contents.

A current supply cord 25 connects through an on-off switch 26 with the lamp. The switch is fixed to the underside of the panel, and its operating arm 27 projects above the surface of the panel.

Mounted upon a fork 28 at the forward end of the panel is a unit 31 (FIGS. 1, 3) for magnifying and viewing the illuminated bottle and its contents. The fork has a vertically depending stem 32 fixed at its lower end to the front end of the panel. The magnifying and viewing unit 31 is pivoted between the upraised arms 33 of the fork. It includes a convex lens 34 clamped in a peripheral frame 35. Ears 36 extending from diametrically opposed sides of the frame pivot upon pins which project inwardly from the arms of the fork and define the horizontal axis of the unit.

The lens 34 is of sufficient diameter, here four inches, to enable viewing through it with both eyes of the examiner. The lens may be manually adjustably pivoted upwardly or downwardly on its axis relative to the illuminated bottle so as to obtain the most favorable enlargement and view of the bottle and its contents for the examiner.

The horizontal axes of the viewing unit 31 and the light source unit 17 are set so as to be at a level above the height of a bottle seated upon the platform 6. This is of advantage in that it enables viewing of the bottle and projecting of the light to be angularly downwardly upon the bottle. In this arrangement, light rays of the lamp are directed away from the eyes of the examiner so as to leave him with a clear vision of the bottle.

FIGS. 6 and 7 show a modification that may be used for mounted the viewing unit 31 upon the panel. The modification provides a keyway or track 37 fixed upon the surface of the panel 1 along the longitudinal axis thereof, and provides the lower end of the stem 32a of the unit with a key 38 engageable in the keyway. This arrangement enables the viewing unit to be adjustably moved along the keyway to any selected position relative to the bottle and platform 6.

In using the invention, a blood culture bottle is injected with a blood specimen and, after a predetermined time interval, the bottle is seated upon the platform 6 for inspection. After the switch is actuated to illuminate the lamp, the light source and viewing units 17, 31 are adjusted and focused upon the bottle to obtain a desired illumination and magnification of it. Then, while closely viewing the illuminated bottle through the magnifying lens, the examiner slowly and intermittently turns the control knob 15 to effect a corresponding turning of the platform 6 and the bottle. In this manner he will progressively bring all areas of the bottle and its contents into view for detection of any bacteria that may have developed therein. This process may be repeated at short intervals until the examiner is satisfied with his findings.

At times, it is desired to simultaneously inspect a pair of blood culture bottles, one of which is aerobic and the other of which is anaerobic, and in each of which a specimen of the same blood has been injected. Because the aerobic bottle contains some oxygen, bacterial growth, if any, will develop more quickly and to a greater degree therein than in the anaerobic bottle.

The simultaneous inspection of both of these bottles is sometimes desired for comparison as well as other purposes. To enable this dual inspection with the instrument of the present invention, an adapter platform 39 (FIG. 5) is utilized. This platform is of rectangular form and adequate in length to permit the pair of bottles 40, 41 (broken line) to be seated thereon. The platform is in the nature of a cover having side walls 42. In use, it is positioned over the existing single bottle platform 6. A set screw 43 in one of the side walls will, when tightened, hold both platforms together, so that rotation of the under platform 6 will carry the adapter platform around with it.

While an embodiment of the invention has been illustrated and described in detail, it is to be expressly understood that the invention is not limited thereto. Various changes of form, design or arrangement may be made in its components without departing from the spirit and scope of the invention. It is my intent, therefore, to claim the invention not only as shown and described but also in all such forms and modifications or equivalents thereof as might be construed to be within the spirit of the invention when considered in the light of the specification, the drawing and the appended claims.

I claim:

1. An instrument for making a direct visual examination of a blood culture bottle, the instrument comprising a supporting panel, a platform mounted on the panel having relative rotation at a fixed level, a manually rotatable control knob mounted on the panel, belt and pulley means drivingly connecting the knob with the platform for transmitting rotary motion of the knob to the platform, the platform serving as a seat adapted to have a blood culture bottle seated thereon, a forked member mounted on the panel in a rearwardly spaced relation to the platform, a light source pivoted on the forked member upon a horizontal axis at a level relative to the blood culture bottle seated on the platform for casting illumination angularly downward upon the platform and bottle, a second forked member mounted on the panel in a forwardly spaced relation to the platform, a combined viewing and magnifying lens pivoted on the second forked member upon a horizontal axis at a level relative to a blood culture bottle seated on the platform to allow to a viewer looking through the lens an angularly directed downward view of the platform and bottle, and the second forked member being swivelled on its mounting for turning about a vertical axis relative to the platform so as to vary the directional illumination of the light source on the bottle.

2. An instrument for making a direct visual examination of a blood culture bottle as in claim 1, wherein the platform has a slightly raised annular lip defining a circular seat for a blood culture bottle, the latter being of clear glass with a flat bottom of a predetermined thickness, the lip serves as a guide for seating of the bottle, and the elevation of the lip is less than the thickness of the bottom of the bottle so that the contents of the bottle is at a level above the lip.

3. An instrument for making a direct visual examination of a blood culture bottle, the instrument comprising: a base; a platform mounted on the base having rotation about a vertical axis through 360° at a fixed level relative to the base; the platform being adapted to have a blood culture bottle seated thereon; a light source means supported on the base rearwardly of the platform for illuminating a bottle seated on the platform; a viewing and magnifying lens means supported on the base forwardly of the platform for magnifying the bottle to a viewer looking through the lens means; the light source means and the viewing and magnifying lens means each having pivotal movement on their respective supports about a horizontal axis at a level above that of the platform and bottle so as to enable them to be focused angularly downward upon the bottle and platform; and manually operable mechanical means mounted on the base for effecting rotation of the platform through 360° relative to the light source means and the viewing and magnifying lens means.

4. An instrument for making a direct visual examination of a blood culture bottle as in claim 3, wherein the manually operable mechanical means is a manipulative knob mounted on the base and pulley and belt means drivingly connecting the knob with the platform.

5. An instrument for making a direct visual examination of a blood culture bottle as in claim 3, wherein the platform is provided with a raised lip for curbing a bottle seated on the platform against displacement, and the lip has an elevation less than the thickness of the bottom end of a bottle seated on the platform.

6. An instrument for making a direct visual examination of a blood culture bottle as in claim 3, wherein a fork is supported on the base, the light source means is pivoted between a pair of upraised arms of the fork for turning about a horizontal axis relative to the platform, and the fork is swivelled on its support for turning about a vertical axis relative to the platform.

7. An instrument for making a direct visual examination of a blood culture bottle as in claim 6, wherein a fork element has a depending stem mounted to the base, and the viewing and magnifying lens means is pivoted between a pair of upraised arms of the fork element for turning about a horizontal axis relative to the platform.

8. An instrument for making a direct visual examination of a blood culture bottle as in claim 7, wherein a keyway track is mounted on the base forwardly of the platform, and the depending stem has a key formation at its bottom end slidably engaged in the track for movement along the track relative to the platform.

9. An instrument for making a direct visual examination of a blood culture bottle as in claim 3, wherein a dual blood culture bottle seating adapter platform is mountable upon the platform mentioned in claim 3 and is fitted with means for securing it to the latter platform for rotation as a unit with it.

10. An instrument for making a direct visual examination of a blood culture bottle, the instrument comprising: a base, a platform mounted on the base having rotation about a vertical axis through 360° at a fixed level relative to the base, the platform being adapted to have a blood culture bottle seated thereon, a manually rotatable knob on the base, a first pin fixed to the knob and depending through the base into a space below the base, a second pin fixed to the platform and depending through the base into the space, pulley and belt means in the space drivingly connecting the first pin with the second pin for effecting on rotation of the knob a corresponding rotation of the platform, a fork supported on the base rearwardly of the platform having swivel movement about a vertical axis, a light source mounted in the fork having a pivotal movement about a horizontal axis for illuminating a bottle seated on the platform accordingly as the fork is swivelled and the light source is pivoted, the mounting of the light source in the fork being at a level above that of the platform and bottle so as to enable the light source to be focused downwardly upon the bottle, a second fork mounted on the base forwardly of the platform, a convex viewing and magnifying lens mounted in the second fork enabling magnification of the bottle and platform to one looking through the lens, and the lens having pivotal movement on its mounting about a horizontal axis at a level above that of the platform and bottle so as to enable the lens to be focused downwardly upon the bottle.

* * * * *